US011065468B2

(12) United States Patent
Barrau et al.

(10) Patent No.: US 11,065,468 B2
(45) Date of Patent: Jul. 20, 2021

(54) OPTICAL DEVICE

(71) Applicant: ESSILOR INTERNATIONAL (COMPAGNIE GENERALE D'OPTIQUE), Charenton le Pont (FR)

(72) Inventors: Coralie Barrau, Charenton-le-Pont (FR); Thierry Villette, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/508,542

(22) PCT Filed: Sep. 2, 2015

(86) PCT No.: PCT/EP2015/070059
§ 371 (c)(1),
(2) Date: Mar. 3, 2017

(87) PCT Pub. No.: WO2016/102083
PCT Pub. Date: Jun. 30, 2016

(65) Prior Publication Data
US 2017/0274221 A1 Sep. 28, 2017

(30) Foreign Application Priority Data
Sep. 3, 2014 (EP) .................................. 14290263

(51) Int. Cl.
A61N 5/06 (2006.01)
G02B 5/22 (2006.01)
G02C 7/10 (2006.01)
G02B 5/28 (2006.01)

(52) U.S. Cl.
CPC ........... A61N 5/0613 (2013.01); G02B 5/223 (2013.01); G02B 5/28 (2013.01); G02B 5/283 (2013.01); G02B 5/285 (2013.01); G02C 7/104 (2013.01); A61N 2005/0662 (2013.01); G02C 2202/10 (2013.01)

(58) Field of Classification Search
CPC combination set(s) only.
See application file for complete search history.

(56) References Cited

U.S. PATENT DOCUMENTS

| 2007/0025118 A1* | 2/2007 | Silver | G02C 11/04 362/552 |
|---|---|---|---|
| 2008/0186448 A1* | 8/2008 | Ishak | G02C 7/104 351/159.6 |
| 2010/0149483 A1* | 6/2010 | Chiavetta | G02B 5/289 351/159.63 |
| 2012/0008217 A1* | 1/2012 | Ishak | A61F 2/1613 359/722 |
| 2014/0055736 A1 | 2/2014 | Ishak | |
| 2014/0233105 A1* | 8/2014 | Schmeder | G01J 3/465 359/590 |
| 2014/0300857 A1* | 10/2014 | Cohen-Tannoudji | G02C 7/104 351/159.63 |
| 2015/0146166 A1* | 5/2015 | Weber | G02C 7/107 351/159.62 |

FOREIGN PATENT DOCUMENTS

| DE | 10 2007 007778 A1 | 6/2008 | |
|---|---|---|---|
| EP | 2 602 653 A1 | 6/2013 | |
| WO | 2007/088312 A1 | 8/2007 | |
| WO | 2010/109154 A1 | 9/2010 | |
| WO | 2012/153072 A1 | 11/2012 | |
| WO | WO 2013084177 A1 * | 6/2013 | ............ G02C 7/104 |
| WO | 2014/133111 A1 | 9/2014 | |

OTHER PUBLICATIONS

International Search Report and Written Opinion of the ISA for PCT/EP2015/070059 dated Jul. 13, 2016, 9 pages.
Schott, "Optical Filters—Glass Filters," Optical Filter Catalogue, Schott Total Customer Care, Jun. 1, 1997, 2 pages, XP007922995.
Corion, "Corion Optical Filters and Coatings," Jan. 1, 1998, vol. 2nd edition, 5 pages, XP007922994.

* cited by examiner

Primary Examiner — Scott Luan
(74) Attorney, Agent, or Firm — Nixon & Vanderhye

(57) ABSTRACT

An optical device including an optical substrate providing with an optical filter configured to inhibit transmission of harmful UV and/or blue light wherein the optical device is further configured to allow retinal exposure of an eye to at least one selected range of wavelengths of light in the visible spectrum of 460 nm to 560 nm, preferably of 480 nm to 520 nm.

12 Claims, 2 Drawing Sheets

OPTICAL DEVICE

FIELD OF THE INVENTION

The invention relates to an optical system, preferably an optical lens, comprising an optical substrate and to the use of such an optical device. Embodiments of the invention relate also to a method of selecting an optical device adapted for a wearer.

BACKGROUND OF THE INVENTION

The discussion of the background of the invention herein is included to explain the context of the invention. This is not to be taken as an admission that any of the material referred to was published, known or part of the common general knowledge at the priority date of any of the claims.

The electromagnetic spectrum covers a wide range of wavelengths, among which are wavelengths visible to the human eye often referred to as the visible spectrum, covering a range of from 380 nm to 780 nm. Some wavelengths of the electromagnetic spectrum including those of the visible spectrum provide harmful effects, while others are known to have beneficial effects on the eye. Some wavelengths of the visible spectrum are also known to induce a range of neuroendocrine, physiological and behavioural responses known as non-image-forming (NIF) responses.

The vertebrate retina is a light-sensitive tissue lining the inner surface of the eye. This tissue has four main layers from the choroid to the vitreous humour: the retinal pigment epithelium, the photoreceptor layer (including rods and cones), the inner nuclear layer with bipolar and amacrine cells, and finally, the ganglion cell layer which contains some intrinsically photosensitive ganglion cells (1 to 3% of retinal ganglion cells (hereinafter referred to as "ipRGC")). Neural signals initiate in the rods and cones, and undergo complex processing by other neurons of the retina. The output from the processing takes the form of action potentials in retinal ganglion cells, the axons of which form the optic nerve. Several important features of visual perception can be traced to the retinal encoding and processing of light.

Light is mostly beneficial for visual and non-visual functions of the eye, including visual perception and circadian functions. Nonetheless, any optical radiation might potentially be hazardous to the eye if it is received and absorbed by the eye tissues at doses capable of causing photomechanical, photothermal or photochemical reactions. If the eye has progressively evolved to protect itself from light-induced damage, adverse changes from both acute and chronic light exposures still exist. Deleterious effects of cumulative UV exposure have been widely evidenced for the cornea and the crystalline lens. Besides, cumulative and prolonged blue-violet exposure (the most energetic part of blue) may significantly induce irreversible retinal photochemical injuries and contribute to the development of early and late age-related maculopathy (ARM), such as Age Related Macular Degeneration (AMD).

During the past 2 decades, empirical proof has evidenced that human physiology and behavior are largely influenced by retinal illumination.

Ophthalmic devices that filter out with low selectivity harmful UV radiations are widely used. For example, sunglasses are designed to provide UV solar protection by protecting the eye against the harmful effects of UVA and UVB rays.

However, sunglasses significantly decrease retinal exposure to visible beneficial light.

The attenuation of visible beneficial light induced by sunglasses may progressively have a detrimental effect on the biological, hormonal and behavioral functions entrained by retinal illumination. A daily repeated and abusively prolonged wearing of sunglasses interferes with the circadian rhythm of the wearer. In long-term, that might induce, for example, sleep troubles, seasonal affective disorders, mood disorders.

Furthermore, by significantly attenuating light intensity, sunglasses increase pupil area with a logarithmic trend. The increase in pupil size which normally accompanies decrease of illumination should enhance to some extent the deleterious effects on visual acuity of the optical aberrations.

Furthermore, the increase in pupil size increases the energetic power of non-filtered wavelengths reaching the retina, particularly the noxious blue-violet wavelengths.

SUMMARY OF THE INVENTION

Accordingly, the present invention aims at overcoming at least one technical problem of the prior art as mentioned above.

In particular, one aim of the invention is to provide an optical device that enhances the protection against harmful light while preserving the beneficial effects of visible daylight.

According to a first aspect of the invention there is provided an optical device comprising an optical substrate providing with an optical filter configured to inhibit transmission of harmful UV and/or blue light wherein the optical device is further configured to allow retinal exposure of an eye to at least one selected range of wavelengths of light in the visible spectrum of 460 nm to 560 nm, preferably of 460 nm to 530 nm, more preferably of 480 nm to 520 nm.

Advantageously, the optical filter is configured to allow transmission in the visible spectrum outside the selected range of wavelengths at visual transmittance rate of 3% to 43% depending on the level of solar protection required.

In some embodiments, the at least one selected range of wavelengths of light is one selected range of wavelengths centered on a wavelength within the range 480 nm to 510 nm.

In some embodiments, the at least one selected range of wavelengths of light is one selected range of wavelengths with a bandwidth in a range from 30 nm to 70 nm.

In some embodiments of the present invention, the optical filter is configured to selectively inhibit transmission of wavelengths of incident light within the range 380 nm to 455 nm, preferably 415 nm to 455 nm, at an inhibition rate within the range 20% to 100%, preferably 60 to 100%.

In some particular embodiments, the optical filter is configured to selectively transmit light within the at least one selected range of wavelengths of light with an average light transmittance value greater than or equal to 50% and preferably, greater than 95% and more preferably equal to 100%.

In an aspect of the invention, the optical filter comprises a dye and/or pigment configured to allow transmission of the at least one selected range of wavelengths of light.

In another aspect of the invention, the optical filter comprises interferential filtering means configured to allow transmission of the at least one selected range of wavelengths of light.

In some embodiments, the optical filter is further configured to selectively transmit light within the range 560 nm to 600 nm with an average light transmittance value greater than or equal to 50% and preferably equal to 100%.

In an embodiment, the optical device further comprises at least a light emitting element which emits light in the at least one selected range of wavelengths of light.

The light emitting element may comprise a combination of monochromatic light emitting diodes with emission peak centered in between 480 and 520 nm.

The present invention further discloses an optical device for use in preventing or treating chronobiological disorders.

The present invention further discloses an optical device for use in controlling the constriction of the pupil of the eye.

The present invention further discloses an optical device for use in eye photoprotection from light damage and glare, while maintaining chronobiological physiology.

The optical device is an optical lens selected among the list of ophthalmic lens, semi-finished lens, contact lens, intraocular lens.

The present invention further discloses a method for selecting an optical device adapted for a wearer comprising at least a step of measuring the effect of several optical devices on the diameter of the pupil of a wearer followed by a step of selecting the optical device for which the wearer's pupil diameter is optimized when wearing the optical system.

According to a further aspect, the invention relates to a computer program product comprising one or more stored sequences of instructions that are accessible to a processor and which, when executed by the processor, causes the processor to carry out the steps of the method according to the invention.

The invention further relates to a computer readable medium carrying one or more sequences of instructions of the computer program product according to the invention.

Furthermore, the invention relates to a program which makes a computer execute the method of the invention.

The invention also relates to a computer-readable storage medium having a program recorded thereon where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

As used herein, the term optical device includes optical lenses comprising an optical substrate such as ophthalmic lenses, semifinished lens, contact lenses, intraocular lenses (IOL), etc. Ophthalmic lenses are meant a lens adapted to a spectacle frame to protect the eye and/or correct the sight. Ophthalmic lenses may be corrective and non-corrective lenses and also shield, masks and other vision devices intended to be worn in front of the eyes. Although ophthalmic optics is a preferred field of the invention, it will be understood that this invention can be applied to other optical devices having an optical substrate, such as for example, windows, automotive and aircraft windshields, films, ophthalmic instrumentation, computer monitors, television screens, telephone screens, multimedia display screens, lighted signs, light projectors and light sources, and the like.

As used herein, an optical substrate is understood to mean an uncoated substrate, generally with two main faces corresponding in the finished ophthalmic lens to the front and rear faces thereof. The bulk is particularly made of an optical transparent material, generally chosen from transparent materials of ophthalmic grade used in the ophthalmic industry, and formed to the shape of an optical device. The optically transparent material may be a mineral or organic glass. Examples of organic glasses are those made of thermoplastic or thermosetting resin. They may be selected form the group comprising polyamides, polyimides, polysulfones, polycarbonates, polyethylene terephthalate, polyurethane, polyacrylate, polymethyl(meth)acrylate, cycloolefin copolymers, homopolymers and copolymers of allyl carbonates of linear or branched aliphatic or aromatic polyols, homopolymers and copolymers of (meth)acrylic acid and esters thereof, homopolymers and copolymers of thio(meth)acrylic acid and esters thereof, homopolymers and copolymers of allyl esters, homopolymers and copolymers of urethane and thiourethane, homopolymers and copolymers of epoxy, homopolymers and copolymers of sulphide, homopolymers and copolymers of disulphide, homopolymers and copolymers of episulfide, copolymer thereof, blend thereof and combinations thereof.

As used herein, the term coating is understood to mean any layer, layer stack or film which may be in contact with the substrate and/or with another coating, for example a sol-gel coating or a coating made of an organic resin. A coating may be deposited or formed through various methods, including wet processing, gaseous processing, and film transfer. The functional coatings classically used in optics may be, without limitation, an impact-resistant and/or adhesion primer, an abrasion-resistant and/or scratch-resistant coating, an water resistant coating, an anti-reflection coating, a polarized coating, a photochromic coating, or an antistatic coating, an anti dust coating, an anti fog coating, an anti soiling coating, a filter coating, an interferential filter, a mirror coating, a tinted coating or a stack made of two or more such coatings, especially an impact-resistant primer coating coated with an abrasion and/or scratch-resistant coating.

Abrasion- and/or scratch-resistant coatings (hard coatings) are preferably hard coatings based on poly (meth) acrylates or silanes. Recommended hard abrasion- and/or scratch-resistant coatings in the present invention include coatings obtained from silane hydrolyzate-based compositions (sol-gel process), in particular epoxysilane hydrolyzate-based composition.

The primer coatings improving the impact resistance and/or the adhesion of the further layers in the end product are preferably polyurethane latexes or acrylic latexes. Primer coatings and abrasion-resistant and/or scratch-resistant coatings may be selected from those described in the application WO 2007/088312.

The antireflection coating, which improves the antireflective properties of the final optical article by reducing the light reflection at the article-air interface over a relatively large range of the visible spectrum, may be any antireflection coating classically used in the optics field, in particular in ophthalmic optics. As is well known, antireflective coatings traditionally comprise a monolayered or a multilayered stack composed of dielectric or sol-gel materials. These are preferably multilayered coatings, comprising layers with a high refractive index (HI, n>1.5) and layers with a low refractive index (LI, n≤1.5).

The structure and preparation of antireflection coatings are described in more details in patent application WO 2010/109154 and WO 2012/153072.

Coatings such as primers, hard coats and antireflection coatings according to the invention may be deposited using methods known in the art, including spin-coating, dip-coating, spray-coating, evaporation, sputtering, chemical vapor deposition and lamination.

As used herein, a coating that is "on" a substrate/coating or which has been deposited "onto" a substrate/coating is defined as a coating that (i) is positioned above the substrate/coating, (ii) is not necessarily in contact with the substrate/coating, that is to say one or more intermediate coating(s) may be interleaved between the substrate/coating and the relevant coating (however, it does preferably contact said substrate/coating), and (iii) does not necessarily completely cover the substrate/coating.

As used herein, retinal exposure refers to light impingement upon the retina of a subject.

BRIEF DESCRIPTION OF THE DRAWINGS

Other aims, features and advantages will be described hereafter in reference to the accompanying exemplary and non-limiting drawings.

DETAILED DESCRIPTION OF THE INVENTION

Figures 1A, 1B, 1C:
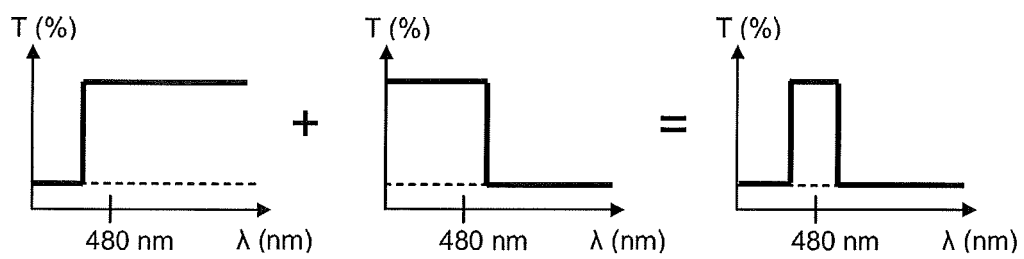
FIG. 1A to 1C illustrate the transmission spectrum of an optical filter provided by one or more embodiments of an optical device according to the invention.
Figure 2:
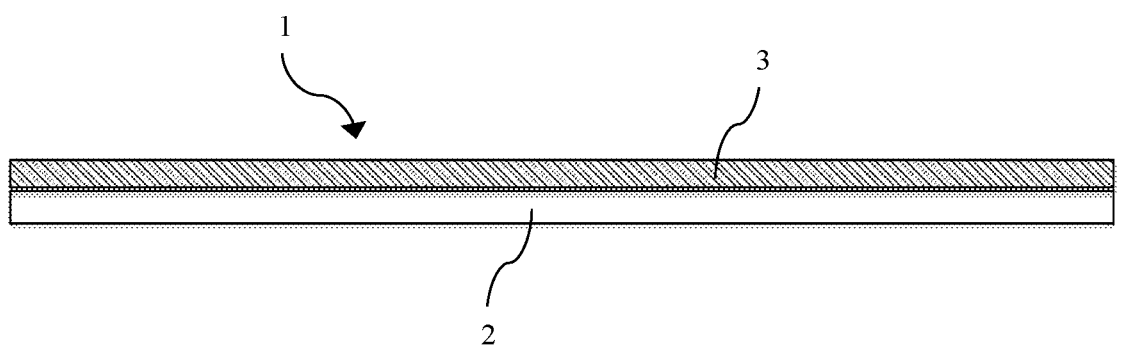
FIG. 2 schematically illustrates an optical device 1 comprising an optical substrate 2 provided with an optical spectral filter 3.

As illustrated in FIG. 1C, an optical device may be used in protecting against harmful light.

In a preferred embodiment, the optical device may be an optical lens.

In one embodiment, the optical device comprises an optical substrate having a first surface and a second surface. In the specific embodiment of an optical lens, the first surface is a concave back/posterior surface, disposed proximal to an eye of a wearer in use and the second surface is a convex front/anterior surface disposed in use distal to the eye.

The optical substrate is provided with an optical filter configured to solar protection and capable of protecting the eyes against harmful ultraviolet (UV) rays.

Additionally or alternatively, the optical device may be used in protecting at least part of an eye of a user from harmful blue light.

The optical filter may be configured to selectively inhibit transmission of wavelengths of incident light within the range 380 nm to 455 nm, preferably 415 nm to 455 nm, at an inhibition rate within the range 20% to 100% and preferably 60% to 100% for an optical lens with solar protection According to the invention, the optical device is furthermore configured to allow retinal exposure of an eye to one or several determined range of wavelengths, one of the range of wavelengths being a selected range of wavelengths of light in the visible spectrum of 460 nm to 560 nm, preferably of 460 nm to 530 nm, more preferably of 480 nm to 520 nm (herewith defined as selected range of wavelength of light).

In preferred embodiments, the selected range of wavelengths of light is centered on a wavelength within the range 480 nm to 510 nm.

With respect to the bandwidth of the selected range of wavelengths, it is within the range from 30 nm to 100 nm, preferably 30 nm to 70 nm.

Said bandwidth are well adapted with the selected range of wavelengths, namely 460 nm to 560 nm, preferably of 460 nm to 530 nm, more preferably of 480 nm to 520 nm.

In a first preferred exemplary embodiment, the range of wavelengths is centered on a wavelength of substantially 480 nm with a bandwidth of 60 nm, preferably 40 nm.

In a second preferred exemplary embodiment, the range of wavelengths is centered on a wavelength of substantially 490 nm with a bandwidth of 60 nm, preferably 40 nm.

In a third preferred exemplary embodiment, the range of wavelengths is centered on a wavelength of substantially 500 nm with a bandwidth of 60 nm, preferably 40 nm.

According to several embodiments of the invention, the retinal exposure of a wearer respective eye may be achieved either by the optical filter configured to allow selectively substantial transmission of the selected range of wavelengths of light or the optical filter or any other light emitting element configured to allow selectively substantial emission of the selected range of wavelengths of light.

Substantial transmission refers to transmission of selected range of wavelength of light with a transmission rate within the range from 50% to 100%, and preferably, greater than 95% or more preferably equal to 100%, so as to provide as much light as possible to a wearer eye.

Substantial emission refers to allowing emission of selected range of wavelength of light with a emission rate in the range from 50% to 100%, preferably, greater than 95% or more preferably equal to 100% so as to provide as much light as possible to a wearer eye.

Furthermore, in a preferred embodiment, the optical filter is configured to enable visual transmittance in the visible spectrum outside the selected range of wavelength of light at 3% to 43% (i.e. at an inhibition rate of 97% to 57%) for example depending on the level of solar protection required such as class 0 to 4 as defined by International standards such as NF EN 1836+A1_2007E or ISO_DIS 12312-1 E.

More precisely, the visual transmittance could be:
- greater than or equal to 18% and smaller than or equal to 43%, so as to provide an optical device adapted for average luminosity environments, or
- greater than or equal to 8% and smaller than or equal to 17%, so as to provide an optical device adapted for high luminosity environments, or
- greater than or equal to 3% and smaller than or equal to 8%, so as to provide an optical device adapted for very high luminosity environments.

In another embodiment, the optical filter is configured to enable transmittance in the visible spectrum outside the selected range of wavelength of light at 80% to 100% (i.e. at an inhibition rate of 20% to 0%)

The optical device according to the invention has several effects on the visual system.

The optical system according to the invention results in an increase of the retinal exposure to a selected range of wavelengths within the blue-green range. The selected range of wavelengths is the best synchronizer of human non visual biological functions.

The inventors have evidenced in a clinical study led in 2013 on 52 young healthy subjects that a 2-week continuous wearing of optical filters cutting off more than 99% of wavelengths comprised between 460 nm and 520 nm is sufficient to induce a 1 hour shift in L5 (five least active hours) and M10 (10 most active hours) sleep-wake criteria.

By optimizing retinal light reception in between 460 nm and 500 nm, we induce the direct stimulation of ipRGC by melanopsin photoreception peaking at 480 nm for humans.

By taking into account the poor spatial density of ipRGC (only 1 to 3% of retinal ganglion cells) compared to that of rod photoreceptors, the probability of absorbing a photon is more than 1 million times lower of a given area of photostimulation. Thus, even if ipRGC phototransduction cascade is highly amplified, the inventors suspect that ipRGCs receive additional input from a complementary photoreception process involving rods. We have observed that ipRGCs may be responsive to lower levels of illumination than initially planned, confirming the role of rods. By extending the transmitted spectral range to 460-530 nm, we induce both the direct stimulation of ipRGC and the indirect stimulation by the incoming rod driven signals peaking near 500 nm.

In particular, this specific illumination range is the most potent stimulus for entraining endogenous rhythms to the daily light cycle with the two photoreceptive processes involved: the melanopsin-driven phototransduction mechanism within the ipRGC itself, peaking near 480 nm and indirect photoreception in rods, peaking near 500 nm.

Therefore, optical devices according to embodiments of the invention may be used in therapy and/or disease prevention.

In particular, optical devices according to embodiments of the invention may be used in therapy for treatment of subjects suffering from chronobiological disorders such as circadian rhythm sleep disorders (jet lag delayed and advanced sleep phase syndroms), hormonal troubles, cognition and memory disorders, psychomotor disorders, body temperature deregulation, mood disorders, alertness disorders, neurobehavioral troubles. Indeed, the optical device according to the invention can compensate inadequate lighting conditions (lack of beneficial blue) to help the biological clock to remain synchronized through the good blue/melatonin secretion relationship. The present invention provides also a method to treat circadian rhythm sleep disorders comprising selectively allowing retinal exposure of an eye to at least one selected range of wavelengths of light in the visible spectrum of 460 nm to 560 nm, preferably of 480 nm to 520 nm.

Additionally or alternatively, optical devices according to embodiments of the invention may be used in therapy to treat seasonal affective disorder (SAD). Symptoms of this disorder can include fatigue, depression, and changes in appetite and sleep patterns. The present invention provides also a method to treat seasonal affective disorders comprising selectively allowing retinal exposure of an eye to at least one selected range of wavelengths of light in the visible spectrum of 460 nm to 560 nm, preferably of 480 nm to 520 nm.

The optical device according to the invention has another beneficial effect on the visual system.

As already indicated, prior art optical devices with solar protection result in an increase of the pupil size.

Advantageously, the inventors have observed that the retinal exposure to the selected range of wavelengths of light of 460 nm to 530 nm, preferably of 480 nm to 520 nm induces maximal pupil constriction by stimulation of ipRGC.

As a consequence of this pupil constriction, the amount of harmful blue-violet light impinged on the retina decreases as a function of the decrease of the pupil diameter (compared to prior art sunglasses), thus limiting retina exposure to noxious wavelengths. This might be particularly advantageously used for children sunglasses and/or workers who work outside at least a part of the day.

Advantageously, the optical device according to the invention provides enhanced protection of the eye against harmful wavelengths (UV and/or blue-violet harmful light) while allowing retinal exposure to beneficial blue-green light.

The optical device to any embodiment of the invention may be configured to enhance the constriction of the pupil of the eye.

In an example, an optical device according to any embodiment of the invention may be used in controlling and enhancing the pupil constriction wherein the selected range of wavelengths of light is centered on a wavelength of substantially 480 nm.

Pupil constriction is wavelength-dependent and is maximal for a light excitation centred at substantially 480 nm, the melanopsin absorption peak.

The present invention provides also a method to control the constriction of the pupil of an eye comprising selectively allowing retinal exposure of an eye to at least one selected range of wavelengths of light in the visible spectrum of 460 nm to 530 nm, preferably of 480 nm to 520 nm.

The invention further provides a method for selecting an optical device according to the invention adapted for a wearer.

The method comprises the steps of measuring the effect of different optical devices according to the invention on the diameter of the pupil of the wearer and of selecting the optical device for which the wearer's pupil diameter is optimized in function of the luminance to have a compromise between visual acuity and chronobiology.

An optical lens with an active system may be used to optimize the wearer's pupil diameter.

In an exemplary embodiment, the method selects the optical device for which the wearer's pupil diameter is minimal when wearing the optical device.

Advantageously, the method according to the invention allows providing the optical device that ensures the greatest protection against harmful wavelengths, i.e. UV and/or blue-violet light.

Furthermore, advantageously, an optical device according to any embodiment of the invention may be used to improve visual acuity of the wearer wearing sunglasses. The decrease in pupil size which accompanies the optical device should reduce to some extent the deleterious effects on visual acuity of the optical aberrations and stray light.

Therefore, the optical device according to the invention enhances the protection against harmful light while preserving the beneficial effects of blue-green part of the sunlight, in particular limiting pupil dilation, maintaining good visual acuity and ensuring the daily blue light intake to maintain good synchronization of biological, hormonal and behavioural functions.

In a second embodiment of the present invention, the optical device is furthermore configured to allow retinal exposure of an eye to a second determined range of wavelengths within 560 nm to 600 nm.

More particularly, the optical filter is further configured to selectively transmit light within the second range 560 nm to 600 nm with an average light transmittance value greater than or equal to 50% and preferably equal to 100%.

Like rhabdomeric opsins of invertebrates, the inventors suggest that melanopsin may be bistable. Retinal absorption of wavelengths comprised between 560 nm to 600 nm, peaking at 580 nm, might be involved in regenerating melanopsin photopigment, thus contributing to an optimized activation of ipRGC.

An optical device according to a first embodiment of the invention will be described with reference to FIGS. 1A to 1C.

According to this embodiment, the optical filter is configured to selectively allow substantial transmission of visible spectrum within the range of 460 nm to 530 nm, preferably of 480 nm to 520 nm, as illustrated in FIG. 1C.

As illustrated in FIG. 1C, the optical filter operates as a bandpass filter selectively allowing transmission, through the optical substrate, from the front surface towards the eye of a user of light, in the selected range of wavelengths, incident on the front surface of the optical lens at the given transmission rate. In one exemplary embodiment, the bandpass filter may be defined with the combination of a short-wave pass filter (FIG. 1A) and a long-wave pass filter (FIG. 1B).

In a non limitative example, the short-wave pass filter partially inhibits transmission of all wavelengths more than 560 nm, preferably more than 530 nm, preferably more than 520 nm, more preferably, more than 500 nm whereas the long-wave pass filter partially inhibits transmission of all wavelengths less than about 460 nm.

In a preferred embodiment, the low short-wave pass filter and the long-wave pass filter are configured to allow the transmission at a given transmittance rate in the range of 3% to 43%.

According to the invention, the optical filter may be obtained through an absorptive filter, an interferential filter or a combination thereof, in order to define the desired light transmittance profile according to the invention.

With respect to selective interference filters, they may be manufactured using interference technologies, such as thin-films, holographic recordings, and any combination thereof.

Thin-film technology uses multiple layers alternating two or more inorganic or hybrid materials with different refractive indices. Each layer may be provided as a coating deposited on the front surface of the base optical substrate by techniques such as sputtering, vacuum evaporation or physical or chemical vapor deposition. A mixed inorganic and organic hybrid stack of layers may be used to optimize the mechanical robustness and curvature compatibility.

According to the invention, the optical filter may be a thin-film made Fabry-Perot bandpass filter, constituted by two dielectric mirrors centered within the range of 480 nm to 510 nm, separated by a cavity or spacer defined as having an optical thickness of a multiple of a half-wave of the central wavelength. The inventors introduce the following notations:

$\lambda 0$ is the central wavelength of the bandpass filter, comprised between 480 nm and 510 nm.

n is the effective refractive index, typically equal or near 3/2 ne is the effective optical thickness

H and L are respectively assigned to high and low refractive index layers of the mirrors, all defined as quarter-wave of the central wavelength $\lambda 0$ C is assigned to the cavity or spacer, defined as half-wave of $\lambda 0$.

Each mirror is for instance defined as follows, with 2n+1 layers:

$$\text{Air}(HL)^n H \text{ Substrate}$$

If n=3/2, four layers between air and substrate are needed to obtain a convenient mirror. Eight layers are needed to obtain a combination of two convenient mirrors.

The stack formula of the complete optical filter is defined as follows:

$$\text{Air}(HL)^n HCH(LH)^n \text{ Substrate}$$

The number of layers is at least equal to 4n+3, i.e. at least 9 layers.

At the selected central wavelength, the matrix defining the stack is the identity matrix, which implies that the filter is transparent with a transmittance equal to that of the substrate. To maximize this transmission at central wavelength, an additional antireflective coating can be added on the optical device.

The optical thickness ne of the cavity is adjusted to obtain a transmittance peak within the range of 480 nm to 510 nm. The bandwidth is inversely proportional to the optical thickness and to the reflectance of the mirrors. One or several cavities may be inserted in between the two mirrors. Preferably, we use only one cavity to ensure a convenient bandwidth comprised between 30 and 70 nm within the selected central wavelengths and a nonzero transmittance outside the selected range of wavelengths.

The high/low refractive index materials may be chosen among the following material couples or any combination thereof, $ZrO_2/SiO_2$, $TiO_2/SiO_2$, $Ta_2O_5/SiO_2$.

The interference filters may be coated on the front face and/or the rear face of the optical substrate such as any functional coating or can be applied onto a functional coating.

With respect to selective absorptive filters, they may comprise as example and without any limitation, dye, pigment, absorber (like UV absorber) and combination thereof known in the art.

The absorptive filter can be applied onto a functional coating of the optical lens, by coating a solution or film lamination thanks to various methods, amongst which are wet processing, gaseous processing, film transfer and lamination process, such as spin-coating, dip-coating, spray-coating, vacuum deposition, evaporation, sputtering, chemical vapour deposition.

Alternatively or additionally, the absorptive filter comprises at least a dye and/or pigment, dispersed within a thermoplastic or thermosetting polymer. The dye and/or pigment may be added to the monomers of the polymer before cross-linking process and then imprisoned within the polymer during cross-linking process.

In one particular example, the thermoplastic or thermosetting polymer comprising the dye and/or pigment is an additional layer applied on the optical lens.

In another particular example, the substrate of the optical lens includes at least one dye and/or pigment.

Depending on the selected range wavelength of transmission, the selective interferential filter as described above may be configured accordingly, or the appropriate choice of absorptive material described above may be made.

The transmission rate of the optical filter in the selected range wavelength of transmission and outside of may be configured according to the use envisaged and/or the level of protection required. The transmission rate may be adjusted by increasing the number of absorptive or interferential layers of the optical filter.

It should be noted that the optical filter may be configured as a passive system or an active system. By passive system it is understood that the optical filter presents a filtering function which cannot be modified or changed. By active system, it is understood that the optical filter provides at least a function that can be modified or changed by an external stimulation such as energy, electrical stimuli, actinic radiation, heating, etc. so that transmission of the selected range of wavelength of light may be switched on or off, or the light transmittance factor varied according to the time of day or the activity of the wearer or the exposure to light.

Furthermore, with respect to the second embodiment of the invention wherein the optical filter is further configured to selectively transmit light within the second range 560 nm to 600 nm, the optical filter operates as a dual band pass filter in order to define the desired light transmittance profile according to the respective embodiment of the invention.

Additionally or alternatively, the inventors propose a third embodiment of an optical device according to the invention.

In this embodiment of the present invention, the optical device comprises a light emitting element configured to allow selectively substantial emission of light in the selected range of wavelengths of 460 nm to 560 nm, preferably of 460 nm to 530 nm, more preferably of 480 nm to 520 nm.

In a preferred embodiment, a combination of monochromatic green light emitting diodes mounted on the optical device, with emission peak centered in between 480 and 520 nm, may be used as illumination element.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. An optical lens configured to be worn by a subject, the optical lens comprising:
    an optical substrate provided with an optical spectral filter configured to inhibit transmission of at least one of UV or blue light by inhibiting transmission of wavelengths from 380 nm to 455 nm at an inhibition rate within a range of 20% to 100%,
    wherein the optical lens that is configured to be worn by the subject is further configured to allow retinal exposure of an eye of the subject through the optical lens to at least one range of wavelengths in visible light spectrum wavelengths of 460 nm to 530 nm, and
    wherein the optical filter is configured to selectively transmit light within the at least one range of wavelengths selected with an average light transmittance value greater than or equal to 50%.

2. The optical lens according to claim 1, wherein the optical filter is configured to allow transmission of visible light spectrum wavelengths outside the at least one range of wavelengths selected at visual transmittance rate of 3% to 43% depending on a level of solar protection required.

3. The optical lens according to claim 1, wherein the at least one range of wavelengths selected is centered on a wavelength within a range 480 nm to 510 nm.

4. The optical lens according to claim 3, wherein the at least one range of wavelengths selected is a range of wavelengths with a bandwidth in a range from 30 nm to 70 nm.

5. The optical lens according to claim 1, wherein the optical filter is configured to selectively inhibit transmission of wavelengths of incident light within a range of 415 nm to 455 nm, at an inhibition rate within a range 20% to 100%.

6. The optical lens according to claim 1, wherein the optical filter comprises at least one of a dye or one pigment configured to allow transmission of the at least one range of wavelengths selected.

7. The optical lens according to claim 1, wherein the optical filter comprises interferential filtering means configured to allow transmission of the at least one range of wavelengths selected.

8. A method for preventing or treating chronobiological disorders, the method comprising:
    exposing an eye of the subject suffering from chronobiological disorders in need thereof to a source of light; and
    positioning the optical lens of claim 1 between the eye of said subject and the source of light so that at least one range of wavelengths selected from visible light spectrum wavelengths from 460 nm to 530 nm is provided to the eye of said subject by the optical device with an average light transmittance value greater than or equal to 50%.

9. A method for controlling the constriction of the pupil of an eye, the method comprising:
    exposing the eye of the subject in need thereof to a source of light; and
    positioning the optical lens of claim 1 between the eye of said subject and the source of light so that at least one range of wavelengths selected from visible light spectrum wavelengths from 460 nm to 530 nm is provided to the eye of said subject by the optical device with an average light transmittance value greater than or equal to 50%.

10. The optical lens according to claim 1, wherein the lens is selected from the group consisting of ophthalmic lens, semi-finished lens, contact lens, and intraocular lens.

11. An optical lens configured to be worn by a subject, the optical lens comprising:
- an optical substrate provided with a single optical filter operating as a Fabry-Pérot bandpass filter constituted by two dielectric mirrors, separated by a cavity having an optical thickness of a multiple of a half-wave of the central wavelength, a central wavelength $\lambda 0$ of the Fabry-Perot bandpass filter being comprised between 480 nm and 510 nm,
- wherein the optical lens configured to be worn by the subject is configured to allow transmission of wavelengths in a range of 460 nm to 530 nm through the optical lens and to inhibit transmission of wavelengths from 380 nm to 455 nm through the optical lens.

12. The optical lens according to claim 11, wherein the optical lens is configured to selectively transmit light within the at least one range of wavelengths selected with an average light transmittance value greater than or equal to 50%.

* * * * *